United States Patent [19]

Zabrowski et al.

[11] Patent Number: 4,992,461
[45] Date of Patent: Feb. 12, 1991

[54] N-AZABICYCLO(3.3.0)OCTANE AMIDES OF AROMATIC ACIDS, COMPOSITIONS, AND METHODS OF USE THEREOF

[75] Inventors: Daniel L. Zabrowski, Skokie; Daniel L. Flynn, Mundelein, both of Ill.

[73] Assignee: G. D. Searle & Co., Chicago, Ill.

[21] Appl. No.: 406,205

[22] Filed: Sep. 11, 1989

[51] Int. Cl.$^5$ .................. C07D 487/04; C07D 403/06; A61K 31/40; A61K 31/405
[52] U.S. Cl. ...................................... 514/413; 548/453
[58] Field of Search ................. 548/453; 514/413, 414

[56] References Cited

U.S. PATENT DOCUMENTS 4,605,662  8/1986  Miyano et al. ...................... 548/453

OTHER PUBLICATIONS

Suri et al., and Ind. J. Chem., vol. 1513, Oct. 1977, pp. 972-973.

Primary Examiner—David B. Springer
Attorney, Agent, or Firm—P. D. Matukaitis; Roger A. Williams

[57] ABSTRACT

A compound of the formula

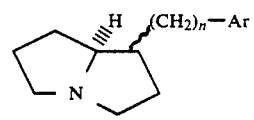

or a pharmaceutically acceptable salt thereof wherein n is 0 or 1; and
Ar is an aromatic amide moiety, which compound exhibits prokinetic activity and is a 5-HT3 antagonist.

50 Claims, No Drawings

N-AZABICYCLO(3.3.0)OCTANE AMIDES OF AROMATIC ACIDS, COMPOSITIONS, AND METHODS OF USE THEREOF

BACKGROUND OF THE INVENTION

The invention herein is directed to novel benzamide compounds and more particularly to azabicyclo[3.3.-0]octane benzamide derivatives.

U.S. Pat. No. 4,213,983 discloses N-(heterocyclic substituted) benzamides which have utility for treating gastrointestinal disorders. The benzamide derivatives have the following general formula:

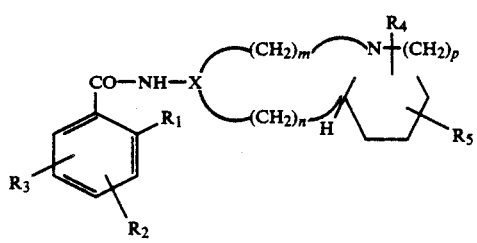

Wherein the heterocyclic moiety is exemplified with respect to bicyclic moieties as 5,6-; 6,6- or 6,5-membered rings wherein n is 1 or 2 and m is 1 or 2 but wherein both n and m are not 1 and X is either a nitrogen atom, in which case m+n is 3 to 5, m is 2 to 4, n is 1 to 3; or X is CH in which case m+n is 2 to 5, m is 1 to 5, and n is 0 to 4.

U.S. Pat. No. 4,808,624 discloses substituted benzamide compounds which are useful in disorders relating to impaired gastric motility. In addition, UK Patent No. 2,152,049 discloses that certain benzamide derivatives exhibit serotonin M antagonistic activity.

Benzamides have been known as 5-HT$_3$ antagonists and as compounds possessing gastrointestinal motility-enhancing properties. Benzamides of the following formula:

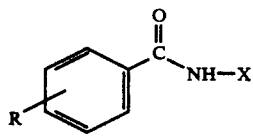

Wherein X can be an azabicycloalkane moiety and which exhibit gastrointestinal motility enhancing and-/or 5-HT$_3$ antagonist properties are disclosed in EP No. 0,094,742A2; EP No. 0,280,603A1; U.S. Pat. No. 4,705,858; U.S. Pat. No. 4,544,660; U.S. Pat. No. 4,797,406; GB No. 2,166,726A; and GB No. 2,145,416A.

European patent publication No. 0,230,718 discloses certain substituted benzamide derivatives, substituted with piperidinyl analogues as having gastrointestinal motility-enhancing and/or antiemetic activity and/or 5-HT receptor antagonist activity.

Indoleamides of the following formula have also been described as possessing gastrointestinal motility-enhancing and/or 5-HT$_3$ antagonist properties:

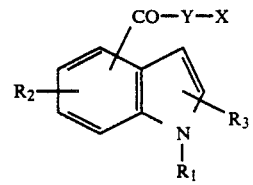

Wherein X contains an aminergic side chain or an azabicycloalkane moiety are described in EP No. 289,170A2; EP No. 297,671A1; EP No. 0,276,163A2; GB No. 2,153,821A; GB No. 2,100,259A; GB No. 2,125,398A; EP No. A-158,265; EP No. A- 200,444; GB No. 2,145,416A; GB No. 2,166,726A; and U.S. Pat. No. 4,797,406.

SUMMARY OF THE INVENTION

The invention herein is directed to compounds of the formula:

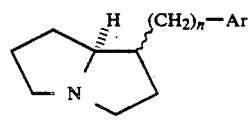

or a pharmaceutically acceptable salt thereof wherein:
n is 0 or 1;
Ar can be

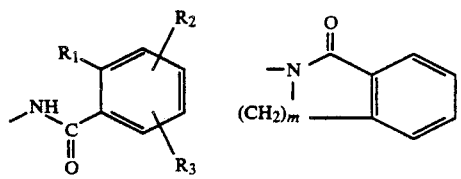

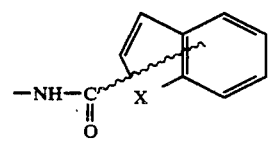

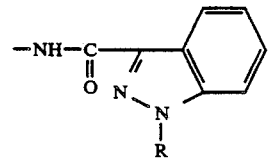

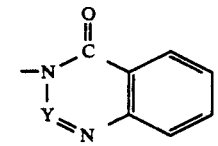

R$^1$ is alkoxy of 1 to 6 carbon atoms; and
R$^2$ and R$^3$ are the same or different and are hydrogen, halogen, CF$_3$, hydroxy, C$_{1-6}$ alkoxy, C$_{2-7}$ acyl, amino, amino substituted by 1 or 2 C$_{1-6}$ alkyl groups, C$_{2-7}$ acyl amino, aminocarbonyl, or aminosulfone optionally substituted by 1 or 2 C$_{1-6}$ alkyl groups, C$_{1-6}$ alkylsulfone or nitro groups;
wherein X can be NR, S, or O;
Y can be CH or N;

R is H, alkyl or aryl; and
m is 1 or 2

A particularly preferred embodiment of the invention herein is a compound of the formula

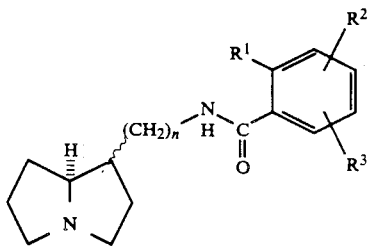

or a pharmaceutically acceptable salt thereof.

The invention herein is also directed to a pharmaceutical composition for the treatment of gastrointestinal disorders comprising a therapeutically effective amount of a compound having any of the above formula or a pharmaceutically acceptable salt thereof.

The invention herein is also directed to a method of treating gastrointestinal disorders by administering to a mammal in need of such a treatment, a therapeutically effective amount of a compound of the formula:

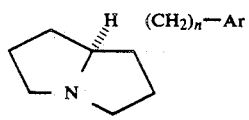

or a pharmaceutically acceptable salt thereof, wherein n is 0 or 1;
Ar can be

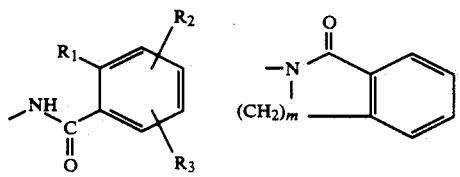

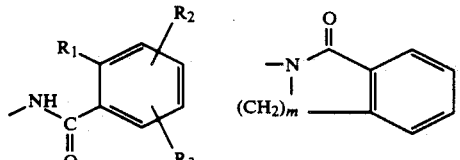

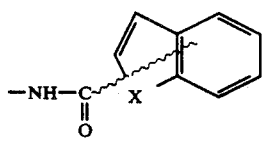

$R_1$ is alkoxy of 1 to 6 carbon atoms;
and $R^2$ and $R^3$ are the same or different, and are hydrogen, halogen, $CF_3$ hydroxy, $C_{1-2}$ alkoxy, $C_{2-7}$ acyl, amino, amino substituted by 1 or 2 $C_{1-6}$ alkyl groups, $C_{2-7}$ acylamino, aminocarbonyl or aminosulfone optionally substituted by 1 or 2 $C_{1-6}$ alkyl groups, $C_{1-6}$ alkylsulfone, or nitro groups;
wherein X can be NR, S, or O;
Y can be CH or N;
R is H, alkyl or aryl; and
m is 1 or 2.

DETAILED DESCRIPTION OF THE INVENTION

The invention herein is directed to compounds of the formula:

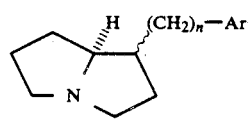

or a pharmaceutically acceptable salt thereof wherein n is 0 or 1;
Ar can be

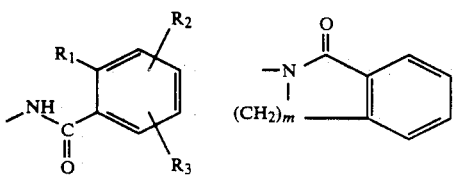

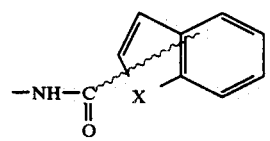

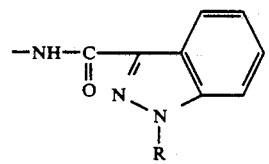

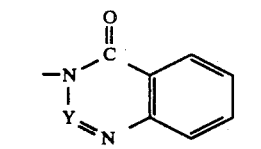

$R^1$ is alkoxy of 1 to 6 carbon atoms; and
$R^2$ and $R^3$ are the same or different and are hydrogen, halogen, $CF_3$, hydroxy, $C_{1-6}$ alkoxy, $C_{2-7}$ acyl, amino, amino substituted by 1 or 2 $C_{1-6}$ alkyl groups, $C_{2-7}$ acylamino, aminocarbonyl or aminosulfone optionally substituted by 1 or 2 $C_{1-6}$ alkyl groups, $C_{1-6}$ alkylsulfone or nitro groups;
wherein X can be NR, S, or O;
Y can be CH or N;
R is H, alkyl or aryl; and
m is 1 or 2.

In the structures and formulas herein, the solid triangular bond representation represents a bond extending outwardly from the plane of the paper on which it is drawn. In a similar manner, the series of dashes of decreasing length are used to represent a bond extending below the plane of the paper on which the structure is drawn. The curved bond representation represents that either stereo optical position is present, that is, the bond can either extend above or below the plane of the paper on which the structure is drawn. A bond drawn across a bond line indicates the bond can be to either adjacent atom of the bond. A bond drawn across a bond of an aromatic ring(s) can be to any available atom on the aromatic ring(s). The term "endo" is used herein to refer to the structure shown in formula (IV) wherein the hydrogen and aromatic side chain are opposed ("trans" to each other) and the term "exo" is used herein to refer to the structure (III) wherein the hydrogen and aromatic side chain are on the same side ("cis" to each other).

Particularly preferred compounds of the invention herein include the stereoisomers having the following formulas:

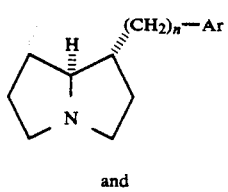

and

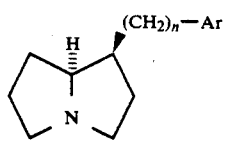

wherein n, Ar, $R^1$, $R^2$ and $R^3$ are defined as above.

More particularly preferred compounds of the invention herein include the stereoisomers having the following formulas:

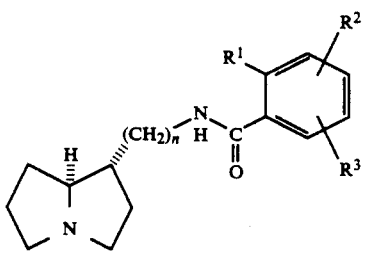

and

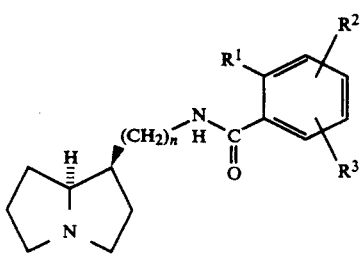

wherein n, $R^1$, $R^2$ and $R^3$ are defined as above. The invention herein is also directed to a method of treating gastrointestinal disorders by administering to a mammal in need of such a treatment, a therapeutically effective amount of a compound of the formula:

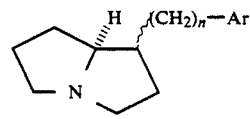

or a pharmaceutically acceptable salt thereof, wherein n is 0 or 1;
Ar can be

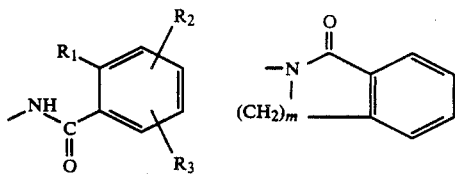

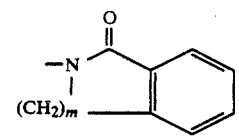

$R_1$ is alkoxy of 1 to 6 carbon atoms;
and $R^2$ and $R^3$ are the same or different, and are hydrogen, halogen, $CF_3$ hydroxy, $C_{1-2}$ alkoxy, $C_{2-7}$ acyl, amino, amino substituted by 1 or 2 $C_{1-6}$ alkyl groups, $C_{2-7}$ acylamino, aminocarbonyl or aminosulfone optionally substituted by 1 or 2 $C_{1-6}$ alkyl groups, $C_{1-6}$ alkylsulfone, or nitro groups;
wherein X can be NR, S, or O;
Y can be CH or N;
R is H, alkyl or aryl; and
m is 1 or 2

The invention herein is also directed to a method of treating gastrointestinal disorders by the step of administering to a mammal in need of such a treatment a therapeutically effective amount of a compound of the formula:

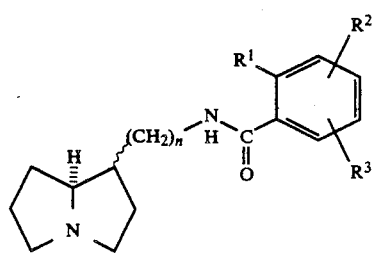

or a pharmaceutically acceptable salt thereof, wherein n is 0 or 1; $R^1$ is alkoxy of 1 to 6 carbon atoms; and $R^2$ and $R^3$ are the same or different and are hydrogen, halogen, $CF_3$, hydroxy, $C_{1-2}$ alkoxy, $C_{2-7}$ acyl, amino, amino substituted by 1 or 2 $C_{1-6}$ alkyl groups, $C_{2-7}$ acylamino, amino carbonyl or aminosulfone optionally substituted by 1 or 2 $C_{1-6}$ alkyl groups, $C_{1-6}$ alkyl sulfone or nitro groups.

The compounds herein are not limited to any particular stereochemical configuration except as shown in the formula. The scope of this invention includes all stereoisomers thereof including diastereomers and individual enantiomers.

Suitable examples of the group $R^1$ include methoxy, ethoxy, and n- and iso-propoxy. Preferably $R^1$ is a methoxy group. Suitable examples of the groups $R^2$ and $R^3$ include the following groups: hydrogen, chlorine, bromine, $CF_3$, hydroxy, methoxy, ethoxy, n- and iso-propoxy, n- and sec- and tert-butoxy, acetyl, propionyl, butyryl, amino, amino substituted by 1 or 2 methyl, ethyl, n- or iso-propyl, n-, sec- or tert-butyl groups, acetylamino, propionylamino, butyramino, aminosulfone, aminosulfone substituted by 1 or 2 methyl, ethyl, n- or iso-propyl, n-, sec- or tert-butyl groups, and methyl, ethyl and n- and and iso-propylsulfones, and nitro, $R^2$ and $R^3$ can also be aminocarbonyl, optionally substituted as for an amino sulfone group.

Particularly suitable $R^2$ and $R^3$ groups include hydrogen, halogen, amino and substituted amino as defined above. The $R^2$ and $R^3$ can be located at any available position on the phenyl group. It is generally preferred that the $R^2$ and $R^3$ groups are located in the 4- and 5-positions relative to the carbonyl side chain for greater activity in the resultant compound of the formula I. For the purposes of distinguishing between $R^2$ and $R^3$ it is preferable that $R^2$ is in the 4-position and $R^3$ is in the 5 position relative to the carbonyl side chain.

Particularly preferred $R^2$ groups include 4-amino and 4-(substituted amino) as defined above. Preferably, $R^2$ is 4-amino. Particularly preferred $R^3$ groups include 5-halo and more particularly 5-chloro.

The pharmaceutically acceptable salts of the compound of the formula I include acid addition salts with conventional acids, such as hydrochloric, hydrobromic, phosphoric, sulphuric, citric, tartaric, lactic, acetic and the like.

The pharmaceutically acceptable salts of the compounds of the formula I also include quaternary ammonium salts. Examples of such salts include salts with compounds such as $R^4$-Z wherein $R^4$ is $C_{1-6}$ alkyl, phenyl-$C_1$-alkyl or $C_{5-7}$ cyclo alkyl, and Z is an ion of an acid. Suitable examples of $R^4$ include methyl, ethyl and n- and iso-propyl; and benzyl and phenyl ethyl. Suitable examples of Z include the halides such as chloride, bromide and iodide.

The compounds herein can be prepared through the reaction sequence which is shown in Scheme 1. With reference to Scheme 1, a bicyclic ester (1) undergoes an aminolysis reaction to form a bicyclic amide (2). Through the nucleophilic substitution reaction occurring during aminolysis, an exo amide (2) and an endo amide (3) form. The two isomers can be separated using column chromatography and the isomers separately reacted as shown in the reaction scheme.

The respective bicyclic amide (2 or 3) can be independently reduced to the respective amines (4) and (5). The amines are reacted with a suitable substituted benzoic acid (6) to form the amides (7 and 8). The respective amides (7 and 8) can undergo a deprotection step wherein the p-acetamide on the benzene ring can be converted to an amine group from the amide forming the compounds (9 and 10).

SCHEME I

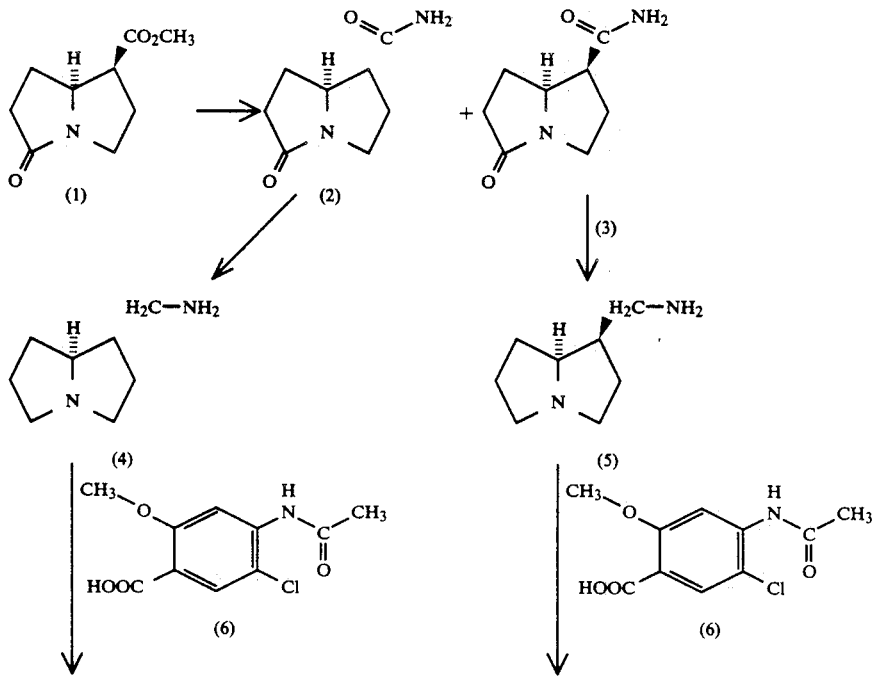

SCHEME 1

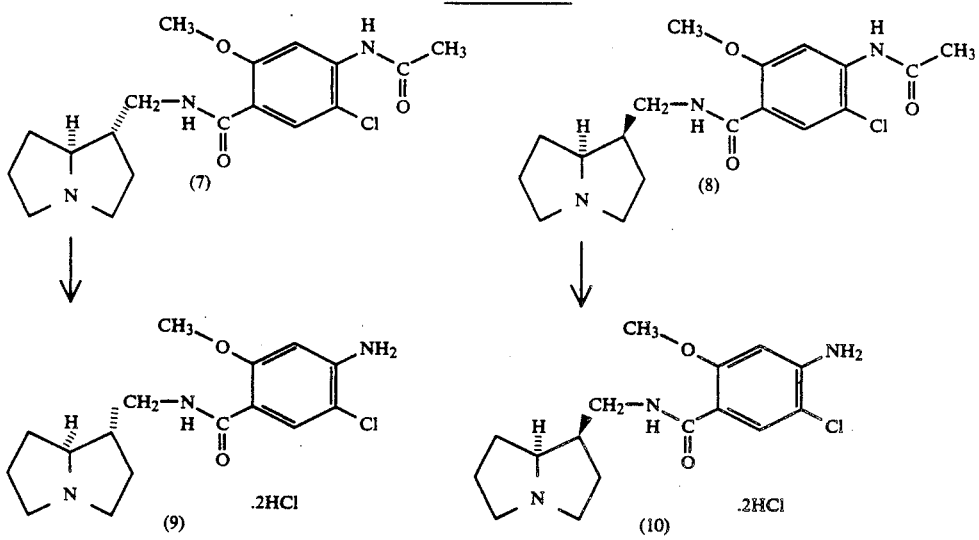

Using the bicyclic amides (2) and (3) from the above reaction Scheme 1 and employing a Hoffman reaction (Ber. 14 (1881), 2725), produces amines (11) and (12) as shown in the following reaction Scheme 2. The amines can be reduced using lithium aluminum hydride which provides the amines (13) and (14). The amines (13) and (14) can undergo reaction with an appropriate aromatic acid in a similar manner as the amines (4) and (5) in Scheme 1 to produce amides of the general formula II wherein n is zero.

The following basic reaction sequence can be followed to produce the amides herein from an aromatic acid. For example, any of the following bicyclic aromatic moieties having a carboxylic group can be used in the reaction sequence: indoles, benzothiophenes, benzofurans, indazoles, 4-oxoquinazolines, and 4-oxobenzotriazines.

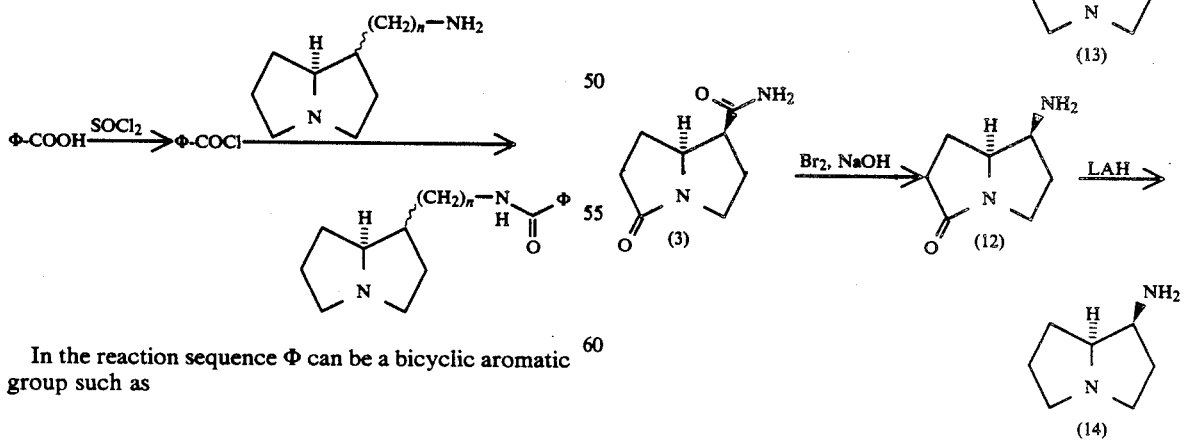

In the reaction sequence Φ can be a bicyclic aromatic group such as

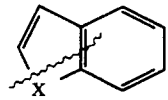

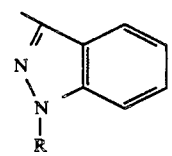

SCHEME 2

A more detailed description of the processes and reactions that are performed to produce the compounds herein are detailed and can be understood through the examples contained later herein.

The compounds disclosed herein can be used in the treatment of mammals exhibiting gastrointestinal motility disorders such as, but not limited to, gastroesophaqeal reflux, delayed gastric emptying, irritable bowel syndrome, diabetic gastroparesis, paralytic ileus, idiopathic pseudoobstruction, functional dyspepsia and the like.

Additionally, compounds of formula I can be useful in the treatment of human disease wherein treatment with a 5-HT$_3$ antagonist is indicated. Thus these compounds possess antiemetic, anxiolytic, anti-psychotic, anti-migraine analgesic, antidiarrheal and colonic motor stimulating properties.

The treatment can be practiced by administering one of the noted compounds or a mixture of such compounds to a mammal in need of such a treatment in a therapeutically effective amount. The compounds can be administered in such oral dosage forms as tablets, capsules, soft gels, pills, powders, granules, elixers, or syrups. The compounds can be administered intravascularly, intraperitoneally, subcutaneously, intramuscularly, or topically, using forms known to the pharmaceutical art. In general, the preferred form of administration is oral or in such a manner as to localize the Prokinetic agent to the gastrointestinal tract. For example, it is possible to administer the compounds via suppository.

For the oral administration of the compounds herein, the compounds are administered in admixture with the suitable pharmaceutical diluents, excipients, or carriers (collectively referred to herein as "carriers") suitably selected with respect to the intended form of administration, that is, oral tablets, capsules, soft gels, elixers, syrups, drops and the like and consistent with conventional pharmaceutical practices.

For example, for oral administration in the form of tablets or capsules, the active drug components can be combined with any oral non-toxic pharmaceutically acceptable inert carrier, such as lactose, starch, sucrose, cellulose, magnesium stearate, dicalcium phosphate, calcium sulphate, mannitol, and the like, or various combinations thereof. For oral administration in liquid forms, such as in soft gels, elixers, syrups, drops, and the like, the active drug components can be combined with any oral, non-toxic pharmaceutically acceptable inert carrier, such as water, saline, ethanol, polyethylene glycol, propylene glycol, corn oil, cottonseed oil, peanut oil, sesame oil, benzyl alcohol, various buffers and the like or various combinations thereof. Moreover, when desired or necessary, suitable binders, lubricants, disintegrating agents, and color agents can also be incorporated in the mixture. Suitable binders include starch, gelatin, natural sugars, corn sweeteners, natural and synthetic gums such as acacia, sodium alginate, carboxymethyl cellulose, carboxyethyl cellulose, polyethylene glycol, and waxes, or combinations thereof. Lubricants for use in these dosage forms include boric acid, sodium benzoate, sodium acetate, sodium chloride and the like, or combinations thereof. Disintegrating agents include, without limitation, starch, methylcellulose, agar, bentonite, guar gum and the like, or combinations thereof. Sweetening and flavoring agents and preservatives can also be included where appropriate.

For intravascular, intraperitoneal, subcutaneous, intramuscular, suppository or aerosol administration, active drug components can be combined with a suitable carrier such as water, saline, aqueous dextrose, and the like. Regardless of the route of administration selected, the compounds described as useful in the method herein can be formulated into pharmaceutically accepted dosage forms by conventional methods known to those skilled in the art. The compounds can be formulated using pharmacologically acceptable salts as described above. Moreover, the compounds or their salts can be used in a suitable hydrated form.

Regardless of the route of administration selected, a non-toxic but therapeutically effective quantity of one or more compounds disclosed herein is employed. The dosage regimen for preventing or treating gastrointestinal motility disorders with the compounds is selected in accordance with a variety of factors, including disorder type, age, weight, sex, and medical condition of the patient, the severity of the gastrointestinal motility disorder, the route of administration, and the particular compound employed in the treatment. A physician or veterinarian of ordinary skill can readily determine and prescribe the effective amount of the compound required to prevent or arrest the progress of the condition. In so proceeding, the physician or veterinarian can employ relatively low doses at first and subsequently increase the dose until a maximum response is obtained.

The following examples are provided to illustrate the preparation of the amide compounds useful herein using the reaction sequence shown in the reaction schemes. The examples herein are given by way of illustration only and are not to be construed as limiting the invention, either in spirit or scope, as modifications, both in materials and methods, will be apparent from this disclosure to those skilled in the art. In these examples, temperatures are given in degrees Celsius (°C.) and quantities of materials in grams and milliliters unless otherwise noted.

EXAMPLE 1

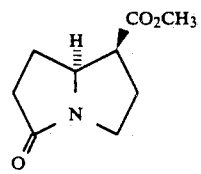

A bicyclic ester of the above formula was prepared by using the method described by Lhommet in *Tetrahedron Letters* 28, 6597 (1987). The bicyclic ester was recovered as endo-6-carbomethoxy-1-azabicyclo[3.3.0]octan-2-one.

EXAMPLE 2

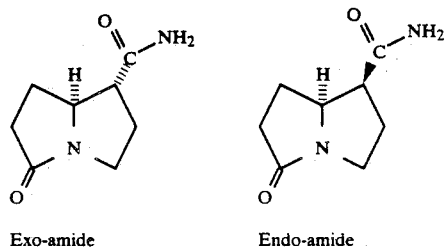

Exo-amide            Endo-amide

A solution of 20.1 g (0.11 mol) of the bicyclic ester from Example 1 in 100 ml of methanol was charged with 100 ml of ammonia. The solution was heated at 50° C. in a Parr bomb for 60 hours. The resulting suspension was concentrated and purified on 3.0 kg of silica gel (chloroform:ethanol:ammonium hydroxide, 90:10:1) to provide 8.8 g of the exo-amide, exo-6-carbamoyl-1-azabicyclo[3.3.0]octan-2-one, of the above formula as a white solid (mp 162.0°-164.0° C.) (ethanol). Found: C 56.92, H 7.33, N 16.67; Theory: C 57.12, H 7.20, N 16.66. Further elution afforded 6.2 g of endo-amide, endo-6-carbamoyl-1-azabicyclo[3.3.0]octan-2-one, of the above formula as a white solid (mp 136.5°-138.0° C.) (ethanol). Found: C 56.92, H 7.19, N 16.56.

EXAMPLE 3

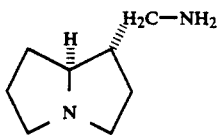

To a suspension of 0.52 g (3.09 mmol) of the exo-amide of Example 2 in 100 ml of tetrahydrofuran was added 18.5 ml (18.5 mmol) of a 1.0 M solution of borane in tetrahydrofuran. The suspension was heated to reflux and vigorously stirred for 18 hours. The solution was cooled, filtered, and acidified with 150 ml of a 10% aqueous solution of hydrochloric acid. After stirring overnight, the clear homogeneous solution was concentrated under reduced pressure. The solid residue was dissolved in 100 ml of water, treated with 100 ml of a 3% aqueous solution of potassium hydroxide and extracted with chloroform (4×125 ml). All organic extracts were combined, dried over anhydrous potassium carbonate, filtered, and concentrated under reduced pressure to produce 0.35 g of the exo-diamine, exo-6-aminomethyl-1-azabicyclo[3.3.0]octane, having the above noted formula as a clear oil.

EXAMPLE 4

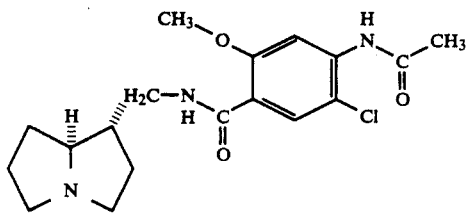

To a suspension of 0.67 g (2.75 mmol) of a substituted benzoic acid (2-methoxy-4-acetamido-5-chlorobenzoic acid) of the following formula:

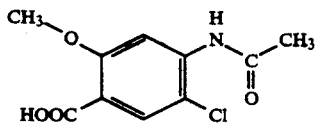

in 40 ml of dimethylformamide was added 0.33 ml (3.0 mmol) of 4-methylmorpholine. After stirring for 30 minutes, 0.36 ml (2.75 mmol) of isobutyl chloroformate was added and was stirred for 2 hours. The resulting yellow solution was treated with a solution of 0.35 g (2.5 mmol) of the diamine from Example 3 in 10 ml of dimethylformamide. The solution was heated to 60° C. and stirred for 26 hours at which time it was concentrated under vacuum. The solid was chromatographed on 150 g (chloroform:ethanol:ammonium hydroxide, 75:25:1) to afford 0.7 g of the acetamide having the above formula as a solid (mp 165.5°-168.0° C. dec.) from ethanol.

EXAMPLE 5

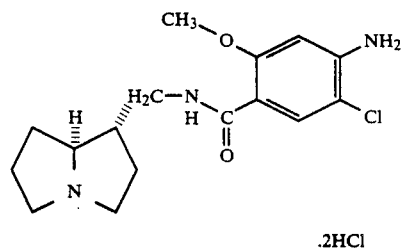

To a solution of 0.7 g (1.91 mmol) of the acetamide from Example 4 in 30 ml of ethanol was added 1.0 g of potassium hydroxide. The solution was heated to reflux and stirred for 2 hours. The solution was concentrated under reduced pressure. The residue was taken up in 100 ml of water and was extracted with chloroform (4×100 ml). The organic extracts were combined, dried over anhydrous potassium carbonate, filtered and concentrated under reduced pressure to produce a residue. This product was dissolved in 35 ml of methanol and exposed to hydrochloric acid gas for 2 minutes. The solution was concentrated under reduced pressure to afford an oil which was dissolved in 10 ml of water and lyophilyzed to provide 0.65 g of dihydrochloride salt as a solid (mp 86.0°-87.0° C.) (isopropanol). cis-4-amino-5-chloro-N-[(hexahydro-1H-pyrrolizin-1-yl)methyl]-2-methoxybenzamide,dihydrochloride Found: C 46.08, H 6.10, N 9.56; Theory: C 45.76, H 6.01, N 9.53.

EXAMPLE 6

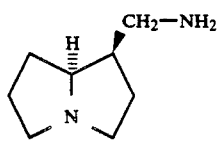

To a suspension of 0.75 g (4.46 mmol) of the endo amide prepared in Example 2 in 200 ml of tetrahydrofuran was added 29 ml (29 mmol) of a 1.0 M solution of borane in tetrahydrofuran. The suspension was heated to reflux and vigorously stirred for 18 hours. The solution was cooled, filtered, and acidified with 250 ml of a 10% aqueous solution of hydrochloric acid. After stirring overnight, the clear homogeneous solution was concentrated under reduced pressure. The solid residue was dissolved in 100 ml of water, treated with 100 ml of a 3% aqueous solution of potassium hydroxide and extracted with chloroform (4×150 ml). All organic extracts were combined, dried over anhydrous potassium carbonate, filtered, and concentrated under reduced pressure to produce 0.5 g of the diamine (endo-6-aminomethyl-1-azabicyclo[3.3.0]octane) having the above formula as a clear oil.

EXAMPLE 7

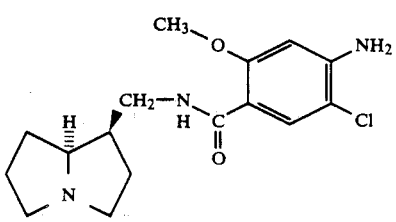

To a suspension of 1.23 g (5.02 mmol) of a substituted benzoic acid (2-methoxy-4-acetamido-5-chlorobenzoic acid) of the formula:

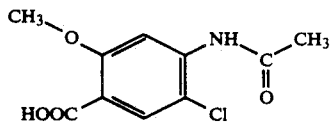

in 40 ml of dimethylformamide was added 0.6 ml (5.48 mmol) of 4-methylmorpholine. After stirring for 30 minutes, 0.65 ml (5.02 mmol) of isobutyl chloroformate was added and was stirred for 2 hours. The resulting yellow solution was treated with a solution of 0.5 g (3.57 mmol) of the Diamine from Example 6 in 5 ml of dimethylformamide. The solution was heated to 60° C. and stirred for 21 hours at which time it was concentrated under vacuum. The solid was chromatographed on 150 g (chloroform:ethanol:ammonium hydroxide, 75:25:1) to afford 1.3 g of an acetamide of the following formula endo-6-[N-(2-methoxy-4-acetamido-5-chlorobenzoyl)aminomethyl]-1-azabicyclo[3.3.0]octane as an amorphous solid:

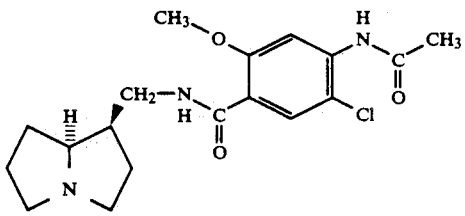

To a warm solution of the acetamide in 100 ml of ethanol was added 4.6 g of potassium hydroxide. The mixture was heated to reflux and stirred for 2 hours. The solution was cooled to room temperature and concentrated under reduced pressure. The residue was taken up in 100 ml of water and extracted with 4 extractions of 100 ml each of chloroform. All organic extracts were combined, dried over anhydrous potassium carbonate, filtered, and concentrated under reduced pressure to afford 0.6 g of crude product as a solid. The solid was dissolved in 100 ml of methanol and exposed to hydrochloric acid gas for 2 minutes to provide the dihydrochloride salt of the above formula, trans-4-amino-5-chloro-N-[(hexahydro-1H-pyrrolizin-1-yl)-methyl]-2-methoxybenzamide,dihydrochloride as a foam. Found: C 47.73, H 6.25, N 9.73; Theory: C 47.47, H 6.37, N 9.49.

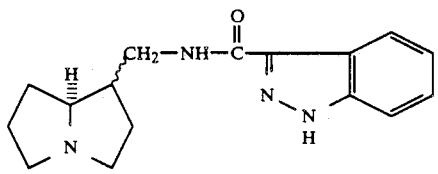

The aromatic acid of the following formula:

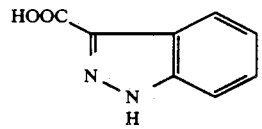

is reacted with thionyl chloride to form an acid chloride. The endo or exo or exo amine (from example 6 or 3 respectively) is reacted with and directly coupled to the acid chloride to provide the respective amine of the above shown formula.

EXAMPLE 9

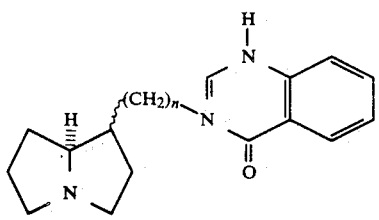

2-Fluorobenzoic acid is reacted with thionyl chloride. An exo or endo amine, prepared in accordance with example 3 or 6 respectively, is reacted with the acid chloride and directly coupled to the amine. Nucleophilic substitution with an amine (or ammonia) affords the 2-aminobenzamide derivative which is treated with an ortho ester to produce the 4-oxoquinoazoline of the respective above formula. The reaction sequence is shown by the following reaction scheme.

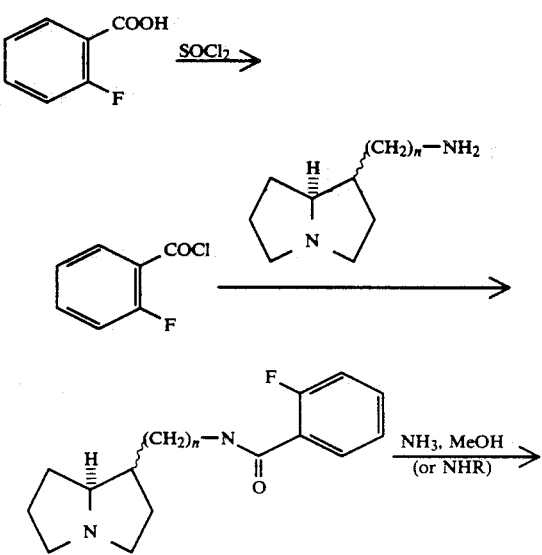

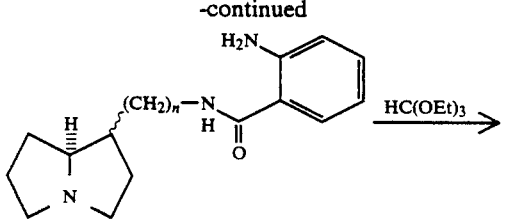

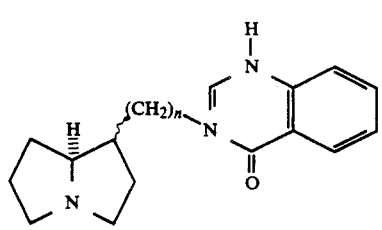

EXAMPLE 10

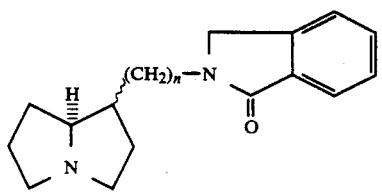

The above compound are prepared by reacting an isothiocyanate (as shown in the below reaction scheme wherein Ts is a tosyl group) with polyphosphoric acid (PPA) followed by basic hydrogen peroxide to give benzolactam (*J. Org. Chem.* 48 (1983), 3229). The benzolactam then can undergo a nucleophilic substitution reaction with the shown endo or exo amine to form an N-substituted benzolactam as shown above.

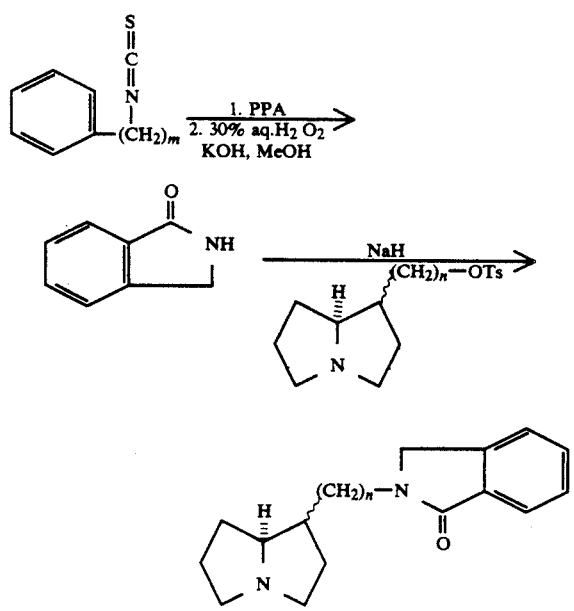

The compounds herein have been shown to be useful for treating gastrointestinal motility disorders in mammals. Their usefulness has been shown by their demonstrated prokinetic activity. Prokinetic activity of a compound can be determined by measuring the enhancement of gastric emptying of a meal in a rat model to which the compound has been administered. This method for determining prokinetic activity of a compound has been described by Droppleman, et al, J. Pharmacol. and Methods 4: 227–230 (1980).

The compounds herein exhibit 5-HT3 antagonism. 5-HT3 antagonism can be determined for a compound by subjecting the compound to a Bezold-Jarisch Reflex test which is described and reported by Saxena, P.R., and Lawang, A.; Arch. Int. Pharmacodyn., 277. 235 (1985). cl Bezold-Jarisch Reflex The test compound is administered i.p. (mg/kg) to a group of 3 mice. Thirty minutes later a 5-HT (0.25 mg/kg i.v.) induced bradycardia is recorded in pentobarbital anesthetized animals. A greater than 50% reduction in the bradycardic response relative to vehicle treated control mice is considered significant. The following Table I shows the results of this test on representative compounds herein and on known 5-HT3 antagonists metoclopramide and cisapride.

TABLE 1

| COMPOUND | DOSE (mg/kg ip) | % INHIBITION |
| --- | --- | --- |
| Example 5 | 10.0 | 85% |
|  | 5.0 | 47% |
| Example 7 | 10.0 | 86% |
|  | 5.0 | 61% |
|  | 2.5 | 55% |
| Metoclopramide | 10.0 | 40% |
| Cisapride | 10.0 | 78% |
|  | 5.0 | 54% |
|  | 2.5 | 49% |

Antiemetic Activity

Antiemetic activity of test compound against cisplatin was determined in beagle dogs. Dogs are pretreated I.V. with a test compound dissolved in DMSO thirty minutes before administration of cisplatin 3 mg/kg.i.v. with a second dose of compounds given i.v. two hours after cisplatin administration. Emetic episodes are counted for 5 hours following cisplatin administration. The latency for first emesis and the number of emetic episodes for test compounds are compared with results for control treatment (vehicle).

Per cent inhibition of emesis for each animal is determined by the following formula:

$$\left( \frac{\text{No. of emetic episodes per treated dog}}{\text{mean no. of emetic episodes all vehicle — treated dogs}} - 1.0 \right) \times 100\% = \%$$

A mean per cent inhibition of emesis is determined for at least 4 dogs.

Antiemetic activity of a representative compound was demonstrated as shown by the results in the following Table II which includes results for metoclopramide, cisapride and ICS 205-930.

TABLE II

| COMPOUND | DOSE (mg/kg iv) | % INHIBITION OF CISPLATIN EMESIS |
| --- | --- | --- |
| Example 5 | 0.3 | 27.0 |
|  | 3.0 | 95.5 |
| Metoclopramide | 0.3 | 19.5 |
|  | 3.0 | 99.9 |
| Cisapride | 0.3 | −2.3 |
|  | 1.0 | 91.0 |

TABLE II-continued

| COMPOUND | DOSE (mg/kg iv) | % INHIBITION OF CISPLATIN EMESIS |
|---|---|---|
| ICS 205-930 | .005 | 60.8 |
|  | .05 | 100.0 |

Rat Gastric Emptying Protocol

A test meal for measuring gastric emptying in rats was prepared. Ten grams of methylcellulose (2% solution=15 centipoises; Aldrich Chemical Company, Milwaukee, Wis.) was added to 200 ml of cold water and mixed at 20,000 rpm in a Waring blender to insure dispersion and hydration of the methylcellulose. In addition, two beef bouillon cubes (Wyler's, Columbus, Ohio) dissolved in 100 ml of warm water was added to the mixture, followed by 16 g of casein (Hammersten, Schwartz/Mann, Orangeburg, N.Y.), 8 g of powdered confectioners sugar and 8 g of cornstarch. The ingredients were mixed for two minutes at 20,000 rpm and the resultant test meal was refrigerated for 48 hours to allow trapped air to escape.

Male Charles River Rats, Crl: COBS, CD (SD) BR Strain, 180-200 g body weight, were used in groups of six animals. The animals were food deprived for 24 hours prior to the experiment with access to water ad libitum. The compounds to be evaluated were prepared in a 0.5% aqueous methylcellulose solution. If insoluble, the mixture was homogenized for two minutes at 5500 rpm using a Try-R-Stir-R. The compounds were injected intraperitoneally at a volume of 5 ml/kg, 30 minutes before the test meal, (3.0 ml/rat i.g.). Control animals received only the vehicle. Sixty minutes after the test meal, the rats were sacrificed by cervical dislocation. The stomachs were removed intact and weighed. The stomachs were kept opened, gently rinsed with tap water, blotted dry with paper towelling, and the empty stomach weighed. The difference between the weight of the full and empty stomach is indicative of the amount of meal remaining in the stomach. The amount of meal remaining in the stomach was subtracted from the weight of 3 ml of the test meal to determine the amount of food emptied from the stomach during the test. Weight of the test meal was determined by weighing three samples (3 ml) at the beginning and three samples at the end of each experiment and calculating the mean. The mean and standard error of the amount of meal emptied were calculated.

The results of following the protocol and comparing representative compounds herein to known prokinetic agents, metoclopramide and cisapride, are shown in Table III.

TABLE III

| COMPOUND | DOSE (mg/kg ip) | % INCREASE IN GASTRIC EMPTYING |
|---|---|---|
| EXAMPLE 5 | 1.0 | 2.5 |
|  | 3.0 | 9.4 |
|  | 10.0 | 15.8 |
| EXAMPLE 7 | 1.0 | 3.1 |
|  | 3.0 | 0.9 |
|  | 10.0 | −6.9 |
| METOCLOPRAMIDE | 1.0 | 2.6 |
|  | 3.0 | 11.2 |
|  | 10.0 | 34.1 |
| CISAPRIDE | 1.0 | 9.8 |
|  | 3.0 | 15.4 |
|  | 10.0 | 25.0 |

Antral Motility in Conscious Fasted Dogs

Gastric antral contractile activity is stimulated by prokinetic drugs which enhance gastric emptying of solid food as has been shown by Jacoby et al, Gastroentrology, 52 676-684 (1967). This contractile activity is thought to enhance gastric emptying by more rapidly reducing food particle size for passage through the pylorus. The ability of a test compound to increase the frequency and/or amplitude of the contractile activity is a measure of gastrointestinal prokinetic activity of the compound.

Mongrel dogs of either sex were surgically implanted with strain gauge force transducers on the gastric antrum at 6 cm, 4 cm and 2 cm from the gastroduodenal junction. The dogs were allowed two weeks to recover and were trained to stand quietly in Pavlov slings.

Dogs were fasted for 18 to 24 hours prior to each experiment to record a pattern of antral contractile activity characteristic of the fasted state called the Migrating Motor Complex (MMC). The period of the MMC cycle is approximately 90 to 120 minutes and consists of 45 to 60 minutes of motor quiescence (Phase I) 30 to 45 minutes of intermittent activity (Phase II) and 10 to 15 minutes of intense contractile activity (Phase III). A control MMC period is recorded prior to compound administration to obtain the length of the quiescent Phase I period. Compound is given intravenously at the end of Phase III of the control MMC cycle and a subsequent Phase I period is examined for the ability of the compound to produce contractions. A response index is calculated as the mean 10 minute motility index for 60 minutes following injection of test compound divided by the 10 minute motility index obtained for the previous Phase III period of the MMC. The response index represents an estimate of the fraction of maximal antral motor activity produced by the compound.

Table IV provides the results of the dog fasted antral motility evaluation of representative compounds herein and known prokinetic agents metoclopramide and cisapride.

TABLE IV

| COMPOUND | DOSE (mg/kg iv) | RESPONSE INDEX |
|---|---|---|
| EXAMPLE 5 | 0.3 | 0.37 |
|  | 1.0 | 0.49 |
|  | 3.0 | 0.58 |
| EXAMPLE 7 | 3.0 | 0.40 |
| METOCLOPRAMIDE | 1.0 | 0.23 |
|  | 3.0 | 0.65 |
| CISAPRIDE | 0.1 | 0.45 |
|  | 0.3 | 0.54 |
|  | 1.0 | 0.41 |

We claim:

1. A compound of the formula

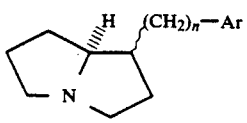

or a pharmaceutically acceptable salt thereof wherein
n is 0 or 1;
Ar can be

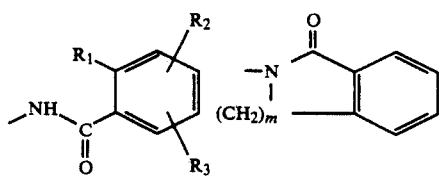

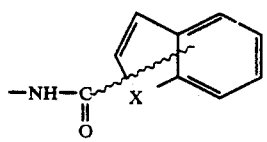

$R^1$ is alkoxy of 1 to 6 carbon atoms; and $R^2$ and $R^3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acylamino, aminocarbonyl or aminosulfone optionally substituted by one or two $C_{1-6}$ alkyl groups, $C_{1-6}$ alkyl sulfone or nitro groups;

wherein X can be NR, S, or O;

R is H, alkyl or aryl; and m is 1.

2. A compound as recited in claim 1 of the formula

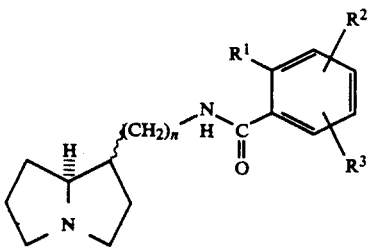

or a pharmaceutically acceptable salt thereof wherein
n is 0 or 1;

$R^1$ is alkoxy of 1 to 6 carbon atoms; and $R^2$ and $R^3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acylamino, aminocarbonyl or aminosulfone optionally substituted by one or two $C_{1-6}$ alkyl groups, $C_{1-6}$ alkyl sulfone or nitro groups.

3. A compound as recited in claim 2 of the formula

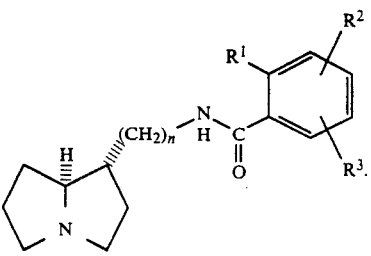

4. A compound as recited in claim 3 wherein n is zero.

5. A compound as recited in claim 3 wherein n is one.

6. A compound as recited in claim 3 wherein $R^1$ is methoxy.

7. A compound as recited in claim 3 wherein $R^2$ is amino.

8. A compound as recited in claim 3 wherein $R^3$ is halogen.

9. A compound as recited in claim 2 of the formula

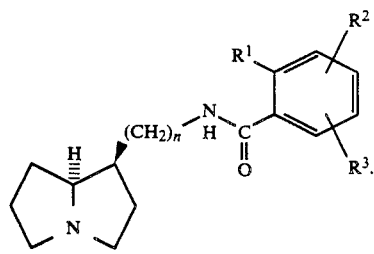

10. A compound as recited in claim 9 wherein n is zero.

11. A compound as recited in claim 9 wherein n is one.

12. A compound as recited in claim 9 wherein $R^1$ is methoxy.

13. A compound as recited in claim 9 wherein $R^2$ is amino.

14. A compound as recited in claim 9 wherein $R^3$ is halogen.

15. A compound as recited in claim 2 wherein $R^1$ is methoxy, $R^2$ is amino and $R^3$ is halogen.

16. A compound as recited in claim 15 of the formula

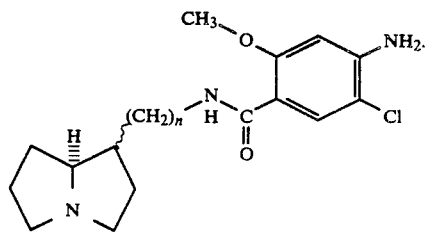

17. A compound as recited in claim 16 of the formula

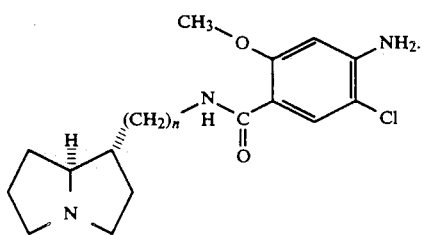

18. A compound as recited in claim 17 where n is one.
19. A compound as recited in claim 16 of the formula

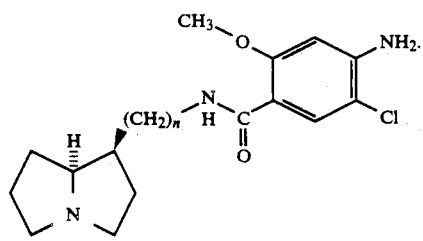

20. A compound as recited in claim 19 wherein n is one.
21. A pharmaceutical composition for the treatment of gastrointestinal disorders or a condition responsive to 5-HT$_3$ antagonism comprising a therapeutically effective amount of a compound of the formula.

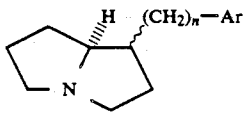

or a pharmaceutically acceptable salt thereof, wherein n is 0 or 1;
Ar can be

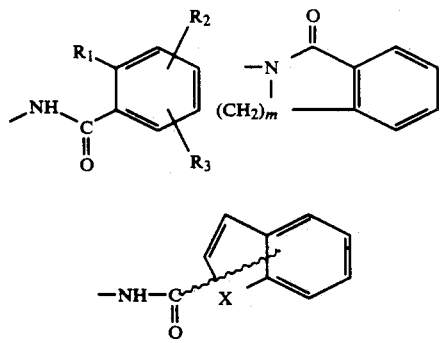

R$^1$ is alkoxy of 1 to 6 carbon atoms; and
R$^2$ and R$^3$ are the same or different and are hydrogen, halogen, CF$_3$, hydroxy, C$_{1-6}$ alkoxy, C$_{2-7}$ acyl, amino, amino substituted by one or two C$_{1-6}$ alkyl groups, C$_{2-7}$ acylamino, aminocarbonyl or aminosulfone optionally substituted by one or two C$_{1-6}$ alkyl groups, C$_{1-6}$ alkyl sulfone or nitro groups;
wherein X can be NR, S or O;
R is H, alkyl or aryl; and
m is 1.

22. A pharmaceutical composition as recited in claim 21 wherein the compound has the formula

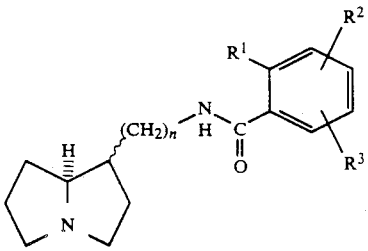

or a pharmaceutically acceptable salt thereof, wherein n is 0 or 1;
R$^1$ is alkoxy of 1 to 6 carbon atoms; and
R$^2$ and R$^3$ are the same or different and are hydrogen, halogen, CF$_3$, hydroxy, C$_{1-6}$ alkoxy, C$_{2-7}$ acyl, amino, amino substituted by one or two C$_{1-6}$ alkyl groups, C$_{1-6}$ alkyl sulfone or nitro groups.

23. A pharmaceutical composition as recited in claim 22 wherein the compound has the formula

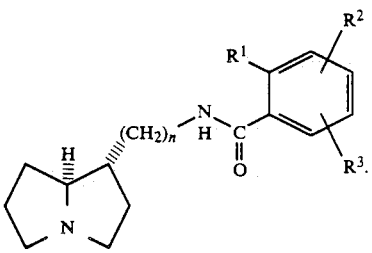

24. A pharmaceutical composition as recited in claim 23 wherein n is zero.
25. A pharmaceutical composition as recited in claim 23 wherein n is one.
26. A pharmaceutical composition as recited in claim 23 wherein n is one, R$^1$ is methoxy, R$^2$ is amino and R$^3$ is halogen.
27. A pharmaceutical composition as recited in claim 22 wherein the compound has the formula

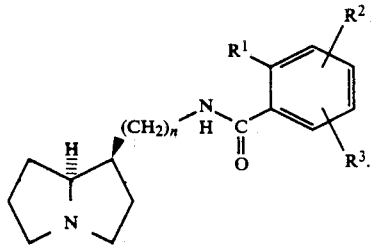

28. A pharmaceutical composition as recited in claim 27 wherein n is zero.
29. A pharmaceutical composition as recited in claim 27 wherein n is one.
30. A pharmaceutical composition as recited in claim 27 wherein n is one, R$^1$ is methoxy, R$^2$ is amino and R$^3$ is halogen.
31. A method of treating gastrointestinal disorders comprising administering to a mammal in need of such treatment a therapeutically effective amount of a compound of the formula

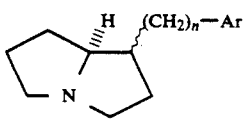

or a pharmaceutically acceptable salt thereof, wherein n is 0 or 1;

Ar can be

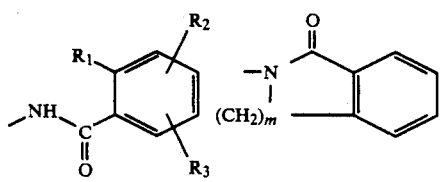

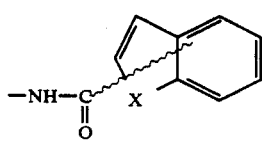

$R^1$ is alkoxy of 1 to 6 carbon atoms; and $R^2$ and $R^3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acylamino, aminocarbonyl or aminosulfone optionally substituted by one or two $C_{1-6}$ alkyl groups, $C_{1-6}$ alkyl sulfone or nitro groups;

wherein X can be NR, S, or O;

R is H, alkyl or aryl; and m is 1.

32. A method as recited in claim 31 wherein the compound has the formula

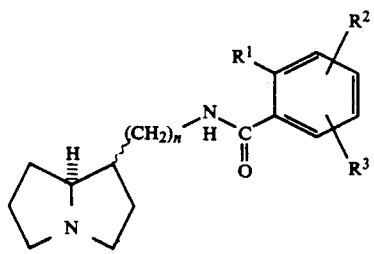

or a pharmaceutically acceptable salt thereof, wherein n is 0 or 1, $R^1$ is alkoxy of 1 to 6 carbon atoms; and $R^2$ and $R^3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acylamino, aminocarbonyl or aminosulfone optionally substituted by one or two $C_{1-6}$ alkyl groups, $C_{1-6}$ alkyl sulfone or nitro groups.

33. A method as recited in claim 32 wherein the compound has the formula

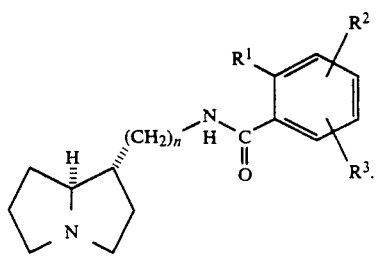

34. A method as recited in claim 33 wherein n is zero.

35. A method as recited in claim 33 wherein n is one.

36. A method as recited in claim 33 wherein n is one, $R^1$ is methoxy, $R^2$ is amino and $R^3$ is halogen.

37. A method as recited in claim 32 wherein the compound has the formula

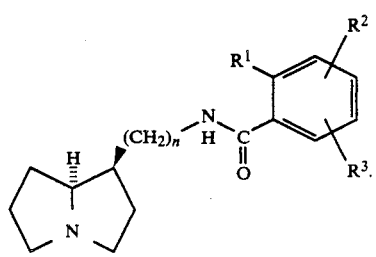

38. A method as recited in claim 37 where n is zero.

39. A method as recited in claim 37 where n is one.

40. A method as recited in claim 37 wherein n is one, $R^1$ is methoxy, $R^2$ is amino and $R^3$ is halogen.

41. A method of treating a condition responsive to 5-HT3 antagonism comprising administering to a mammal in need of such treatment a therapeutically effective amount of a compound of the formula

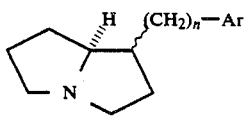

or a pharmaceutically acceptable salt thereof, wherein n is 0 or 1

Ar can be

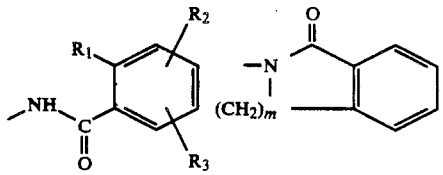

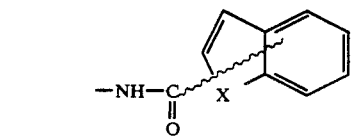

$R^1$ is alkoxy of 1 to 6 carbon atoms; and $R^2$ and $R^3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acylamino, aminocarbonyl or aminosulfone optionally substituted by one or two $C_{1-6}$ alkyl groups, $C_{1-6}$ alkyl sulfone or nitro groups.

wherein X can be NR, S, or O;

R is H, alkyl or aryl; and m is 1.

42. A method as recited in claim 41 wherein the compound has the formula

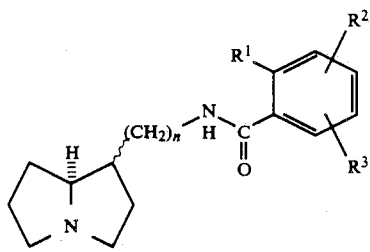

ps or a pharmaceutically acceptable salt thereof, wherein n is 0 or 1

$R^1$ is alkoxy of 1 to 6 carbon atoms; and $R^2$ and $R^3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-7}$ acylamino, aminocarbonyl or aminosulfone optionally substituted by one or two $C_{1-6}$ alkyl groups, $C_{1-6}$ alkyl sulfone or nitro groups.

43. A method as recited in claim 42 wherein the compound has the formula

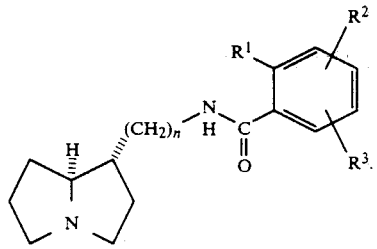

44. A method as recited in claim 43 wherein n is zero.

45. A method as recited in claim 43 wherein n is one.

46. A method as recited in claim 43 wherein n is one, $R^1$ is methoxy, $R^2$ is amino and $R^3$ is halogen.

47. A method as recited in claim 42 wherein the compound has the formula

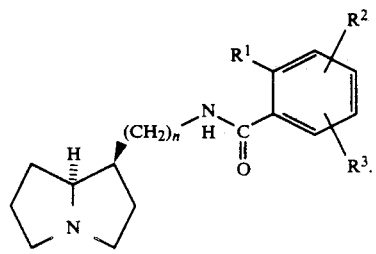

48. A method as recited in claim 47 wherein n is zero.

49. A method as recited in claim 47 wherein n is one.

50. A method as recited in claim 47 wherein n is one, $R^1$ is methoxy, $R^2$ is amino and $R^3$ is halogen.

* * * * *

UNITED STATES PATENT AND TRADEMARK OFFICE
CERTIFICATE OF CORRECTION

PATENT NO. : 4,992,461

DATED : Feb. 12, 1991

INVENTOR(S) : Zabrowski, et. al.

It is certified that error appears in the above-identified patent and that said Letters Patent is hereby corrected as shown below:

Column 8, line 34, SCHEME I reading

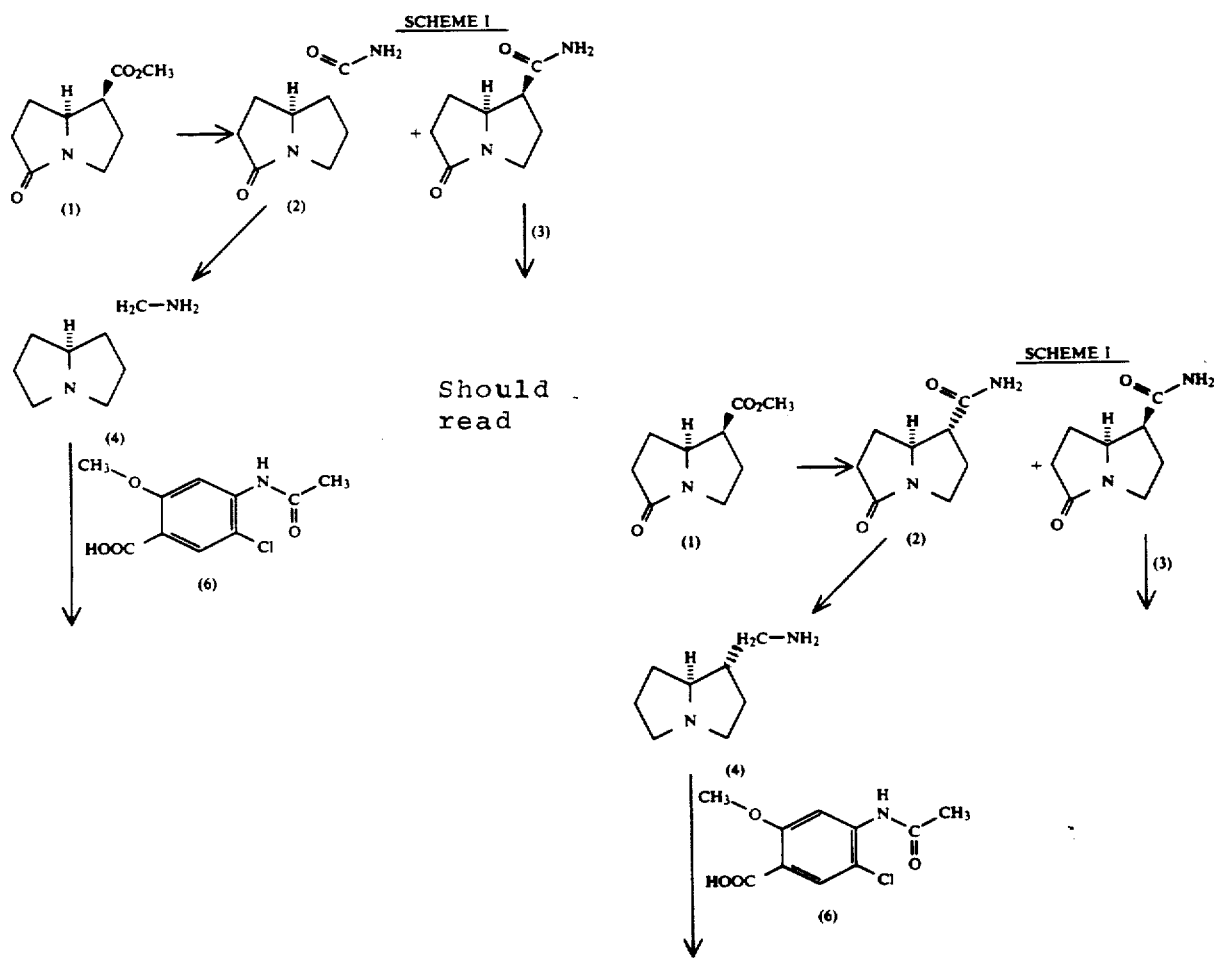

Should read

UNITED STATES PATENT AND TRADEMARK OFFICE
CERTIFICATE OF CORRECTION

PATENT NO.　：　4,992,461

DATED　　　：　Feb. 12, 1991

INVENTOR(S)：　Zabrowski, et. al.

It is certified that error appears in the above-identified patent and that said Letters Patent is hereby corrected as shown below:

Column 11, line 25, reads "Prokinetic agent" should read -- prokinetic agent --.

Column 18, line 11, reads "cl $_{Bezold}$ -Jarisch Reflex" is a title and should read -- $_{Bezold}$ Jarisch Reflex --.

Signed and Sealed this

Twenty-sixth Day of January, 1993

Attest:

STEPHEN G. KUNIN

Attesting Officer　　　　Acting Commissioner of Patents and Trademarks